United States Patent
Yang et al.

(10) Patent No.: US 10,143,368 B2
(45) Date of Patent: Dec. 4, 2018

(54) VISUAL ACUITY TEST METHOD, APPARATUS AND SYSTEM

(71) Applicant: Boe Technology Group Co., Ltd., Beijing (CN)

(72) Inventors: Li Yang, Beijing (CN); Yefei Dong, Beijing (CN)

(73) Assignee: Boe Technology Group Co., Ltd., Beijing (CN)

( * ) Notice: Subject to any disclaimer, the term of this patent is extended or adjusted under 35 U.S.C. 154(b) by 0 days.

(21) Appl. No.: 14/913,283

(22) PCT Filed: Sep. 14, 2015

(86) PCT No.: PCT/CN2015/089520
§ 371 (c)(1),
(2) Date: Feb. 19, 2016

(87) PCT Pub. No.: WO2016/165272
PCT Pub. Date: Oct. 20, 2016

(65) Prior Publication Data
US 2017/0055826 A1    Mar. 2, 2017

(30) Foreign Application Priority Data
Apr. 17, 2015  (CN) .......................... 2015 1 0185244

(51) Int. Cl.
*A61B 3/032* (2006.01)
*A61B 3/00* (2006.01)

(52) U.S. Cl.
CPC ............ *A61B 3/032* (2013.01); *A61B 3/0025* (2013.01); *A61B 3/0041* (2013.01)

(58) Field of Classification Search
CPC ....... A61B 3/028; A61B 3/032; A61B 3/0025; A61B 3/0033; A61B 3/0041
(Continued)

(56) References Cited

U.S. PATENT DOCUMENTS 5,592,247 A * 1/1997 Trokel ................... A61B 3/032
                                                                351/239
5,877,841 A   3/1999 Jeon
(Continued)

FOREIGN PATENT DOCUMENTS

CN   201005675   1/2008
CN   102068234   5/2011
(Continued)

OTHER PUBLICATIONS

"Eye and Vision Assessment in Primary Health Care", BrienHolden Vision Institute, 2013.*
(Continued)

*Primary Examiner* — Jordan Schwartz
(74) *Attorney, Agent, or Firm* — Calfee, Halter & Griswold LLP (57) ABSTRACT

A visual acuity test method, apparatus and system that may be utilized as an automatic test of the visual acuity level of a test object, to reduce the problem of complex operation of the existing visual acuity test solution. The method is applied by an apparatus with a display screen, and comprises: displaying a test picture including at least one optotypes on a display screen, and determining an active optotype for visual acuity test from the optotypes of the test picture according to a preset rule. The method includes the steps of obtaining indicating information of the test object for the active optotype of the test picture; and determining the visual acuity level of the test object according to orientations represented by active optotypes of at least one test pictures and the indicating information of the visual acuity test object for the active optotypes of at least one test picture.

14 Claims, 6 Drawing Sheets

(58) Field of Classification Search
USPC .................................................. 351/237, 239
See application file for complete search history.

(56) References Cited

U.S. PATENT DOCUMENTS

| | | | | |
|---|---|---|---|---|
| 9,066,667 | B1* | 6/2015 | Berme | A61B 3/0033 |
| 2006/0244915 | A1* | 11/2006 | Clemons | A61B 3/032 |
| | | | | 351/245 |
| 2008/0204662 | A1 | 8/2008 | Kanazawa et al. | |
| 2008/0309879 | A1* | 12/2008 | Hirji | A61B 3/032 |
| | | | | 351/223 |
| 2010/0253913 | A1 | 10/2010 | Artal Soriano et al. | |
| 2011/0157180 | A1* | 6/2011 | Burger | G06T 3/00 |
| | | | | 345/428 |
| 2012/0050685 | A1* | 3/2012 | Bartlett | A61B 3/0033 |
| | | | | 351/223 |
| 2012/0057007 | A1* | 3/2012 | Ishiguro | A61B 3/032 |
| | | | | 348/61 |

FOREIGN PATENT DOCUMENTS

| | | |
|---|---|---|
| CN | 102599879 | 7/2012 |
| CN | 102631186 | 8/2012 |
| CN | 102984344 | 3/2013 |
| CN | 203059655 | 7/2013 |
| CN | 203576469 | 5/2014 |
| CN | 104116491 | 10/2014 |
| CN | 104739363 | 7/2015 |
| JP | 2005296382 | 10/2005 |

OTHER PUBLICATIONS

Office action from Chinese Application No. 201510185244.6 dated Jun. 3, 2016.
Office action from Chinese Application No. 201510185244.6 dated Mar. 15, 2016.
International Search Report and Written Opinion from PCT/CN15/89520 dated Jan. 11, 2016.
Office action from Chinese Application No. 201510185244.6 dated Nov. 26, 2015.

* cited by examiner

VISUAL ACUITY TEST METHOD, APPARATUS AND SYSTEM

RELATED APPLICATIONS

The present application is the U.S. national phase entry of PCT/CN2015/089520 with an International filing date of Sep. 14, 2015, which claims the benefit of Chinese Application No. 201510185244.6, filed Apr. 17, 2015, the entire disclosures of which are incorporated herein by reference.

TECHNICAL FIELD

The invention refers to a technical field of medical test, and in particular to a visual acuity test method, apparatus and system.

BACKGROUND

Traditional visual acuity tests are all performed by the subject indicating the orientation of the letters on the visual acuity test chart. The existing visual acuity test charts used are normally visual acuity charts printed. Moreover, it is also required that, the lighting of the environment for the visual acuity test is enough. Thus, for improving the lighting condition of the visual acuity test chart, the visual acuity test chart may be fixed on a surface of a light box to form a chart box, for visual acuity testing. Besides, the existing visual acuity tests all need a tester to point manually on the test chart or chart box.

If the pointing position is not explicit when the tester manually points on the test chart or chart box, the problem of the obtained test result being incorrect easily occurs; at the same time, since pointing manually is needed, it is troublesome to operate in effect and the labor cost is relatively large.

SUMMARY

Embodiments of the invention provides a visual acuity test method, apparatus and system, realizing an automatic test of visual acuity level, reducing the problem of complex operation of the existing visual acuity test schemes.

For realizing the above objects, embodiments of the invention employ the following technical solutions:

In a first aspect, a visual acuity test method is provided, which comprises the steps of:

display a test picture which includes at least one optotypes on a display screen, and determine an active optotype for visual acuity test from the optotypes of the test picture according to a preset rule; obtain indicating information of the visual acuity test subject for the active optotype of the test picture; determine the visual acuity level of the visual acuity test subject according to orientations represented by active optotypes of at least one test pictures and the indicating information of the visual acuity test subject for the active optotypes of the at least one test pictures.

According to a preferred embodiment, before the step of displaying the test picture on the display screen, the method further comprises: obtain a first distance between the visual acuity test subject and the display screen;

the step of displaying the test picture on the display screen comprises: according to a preset standard proportional relation and the first distance, display a test picture with a size corresponding to the first distance on the display screen; the preset standard proportional relation includes: a standard distance between the visual acuity subject and the display screen, and a standard test picture size corresponding to the standard distance.

According to a preferred embodiment, at least two test pictures are included, each of which corresponds to a different visual acuity level.

According to a preferred embodiment, the step of determining the visual acuity level of the visual acuity test subject according to orientations represented by active optotypes of at least one test pictures and the indicating information of the visual acuity test subject for the active optotypes of the at least one test pictures comprises:

Determine whether the indicating information of the visual acuity test subject for the active optotypes in a first test picture of the at least two test pictures matches with the orientation represented by the active optotype in the first test picture;

If the indicating information of the visual acuity test subject for the active optotypes in a first test picture of the at least two test pictures matches with the orientation represented by the active optotype in the first test picture, determine whether the indicating information of the visual acuity test subject for the active optotypes in a second test picture of the at least two test pictures matches with the orientation represented by the active optotype in the second test picture; the second test picture is a test picture having a visual acuity level different from that of the first test picture by N visual acuity levels, and the visual acuity level of the second test picture is higher than that of the first test picture, the N being a positive integer;

If the indicating information of the visual acuity test subject for the active optotypes in the second test pictures does not match with the orientation represented by the active optotype in the second test picture, determine whether the indicating information of the visual acuity test subject for the active optotypes in a third test picture of the at least two test pictures matches with the orientation represented by the active optotype in the third test picture; the third test picture is a test picture having a visual acuity level adjacent with that of the second test picture, and the visual acuity level of the third test picture is lower than that of the second test picture;

If the indicating information of the visual acuity test subject for the active optotypes in the third test pictures matches with the orientation represented by the active optotype in the third test picture, determine the visual acuity level to which the third test picture corresponds as the visual acuity level of the visual acuity test subject.

According to a preferred embodiment, the method further comprises, if the indicating information of the visual acuity test subject for the active optotypes in the third test pictures of the at least two test pictures matches with the orientation represented by the active optotype in the third test picture, perform M times of test circularly with the second test picture and the third test picture, determine a test picture matched by the visual acuity test subject more times in the second test picture and the third test picture, M being a natural number; determine the level to which the test picture matched by the visual acuity test subject more times corresponds as the visual acuity level of the visual acuity test subject.

According a further preferred embodiment, the method further comprises, if the indicating information of the visual acuity test subject for the active optotypes in the first test picture does not match with the orientation represented by the active optotype in the first test picture, then determine whether the indicating information of the visual acuity test subject for the active optotypes in a fourth test picture of the at least two test pictures matches with the orientation represented by the active optotype in the fourth test picture; the fourth test picture is a test picture having a visual acuity level different from that of the first test picture by P visual acuity levels, and the visual acuity level of the fourth test picture is lower than that of the first test picture, the P being a negative integer;

If the indicating information of the visual acuity test subject for the active optotypes in the fourth test pictures matches with the orientation represented by the active optotype in the fourth test picture, determine whether the indicating information of the visual acuity test subject for the active optotypes in a fifth test picture of the at least two test pictures matches with the orientation represented by the active optotype in the fifth test picture; the fifth test picture is a test picture having a visual acuity level adjacent with that of the fourth test picture, and the visual acuity level of the fifth test picture is higher than that of the fourth test picture;

If the indicating information of the visual acuity test subject for the active optotypes in the fifth test pictures does not match with the orientation represented by the active optotype in the fifth test picture, determine the visual acuity level to which the fourth test picture corresponds as the visual acuity level of the visual acuity test subject.

According to a further preferred embodiment, the method further comprises, if the indicating information of the visual acuity test subject for the active optotypes in the fifth test pictures does not match with the orientation represented by the active optotype in the fifth test picture, then perform M times of test circularly with the fourth test picture and the fifth test picture, determine a test picture matched by the visual acuity test subject more times in the fourth test picture and the fifth test picture;

determine the level to which the test picture matched by the visual acuity test subject more times corresponds as the visual acuity level of the visual acuity test subject.

According to a further preferred embodiment, M=2 or 3.

According to a preferred embodiment, the method further comprises before the step of obtaining the first distance between the visual acuity test subject and the display screen, detect whether the visual acuity test subject wears glasses; if it is detected that the visual acuity test subject wears glasses, terminate the test process.

According to a preferred embodiment, if the active optotypes are multiple, display the active optotypes individually on the display screen according to a preset order.

According to a further preferred embodiment, the preset order is adjustable freely.

According to a preferred embodiment, if the active optotypes are multiple, display the active optotypes simultaneously on the display screen, and display a test order identifier on the display screen; the indicating information includes an information indicated in order by the visual acuity test subject for the active optotypes in the test pictures according to the direction indicated by the test order identifier.

According to a preferred embodiment, when the active optotype is determined, make the active optotype at a highlight state, and make the other inactive optotypes at a un-highlight state; alternatively, when the active optotype is determined, make the active optotype and the other optotypes all at a highlight state, and prominently display the active optotype with a regular graph such as a circle, a square, a rectangle etc. or an irregular graph, to differ from the other inactive optotypes.

In another aspect, a visual acuity test apparatus is proposed, which comprises: a display unit, for displaying a test picture which includes at least one optotypes; a processing unit, for determining an active optotype for visual acuity test from the optotypes of the test picture according to a preset rule; a obtaining unit, for obtaining indicating information of the visual acuity test subject for the active optotype of the test picture; the processing unit is further used for determine the visual acuity level of the visual acuity test subject according to orientations represented by active optotypes of at least one test pictures and the indicating information of the visual acuity test subject for the active optotypes of the at least one test pictures.

According to a preferred embodiment, the apparatus further comprises: a ranging unit, for obtaining a first distance between the visual acuity test subject and the display screen before the display unit displaying the test picture; a picture adjusting unit, for adjusting the test picture as a test picture with a size corresponding to the first distance according to a preset standard proportional relation and the first distance;

Therein, the display unit is further used for displaying the test picture with a size corresponding to the first distance; the preset standard proportional relation includes: a standard distance between the visual acuity subject and the display screen, and a standard test picture size corresponding to the standard distance.

According to a preferred embodiment, the apparatus further comprises: a recognizing unit, for detecting whether the visual acuity test subject wears glasses before the ranging unit obtaining the first distance between the visual acuity test subject and the display screen; therein, the processing unit is further used for if the recognizing unit detects that the visual acuity test subject wears glasses, controlling the visual acuity apparatus to stop working.

In another aspect, a visual acuity test system is proposed, which comprises any one of the above visual acuity test apparatus, and an indicating unit for sending the indicating information of the visual acuity test subject for the active optotypes of the at least one test pictures to the visual acuity test apparatus.

The visual acuity test method, apparatus and system proposed by the embodiments of the invention display a test picture on a display screen, and determine an active optotype for visual acuity test from the optotypes of the test picture according to a preset rule, obtains indicating information of the visual acuity test subject for the active optotype of the test picture, and determine the visual acuity level of the visual acuity test subject according to orientations represented by active optotypes of at least one test pictures and the indicating information of the visual acuity test subject for the active optotypes of the at least one test pictures. Compared to the prior art, the visual acuity test apparatus of the embodiment of the invention does not need adding specialized tester additionally, and may realize an automatic test of the visual acuity level of the visual acuity test subject only according to the represented orientation of the active optotype of the displayed test picture and the indicating information of the visual acuity test subject for the active optotype, solving the problem of complex operation of the existing visual acuity test solution.

BRIEF DESCRIPTION OF FIGURES

In order to describe the technical solutions in embodiments of the invention or the prior art more clearly, the figures required for description of the embodiments or prior art will be introduced in brief below. Obviously, the figures in the following only illustrate some embodiments of the invention, and for those skilled in the art, other figures can be obtained from these figures without expending creative effort.

FIG. 5(*a*) is a flow schematic diagram of another visual acuity test method provided by an embodiment of the invention;

FIG. 5(*b*) is a flow schematic diagram of another visual acuity test method provided by an embodiment of the invention;

DETAIL EMBODIMENTS

The solutions in the embodiments of the invention will be described clearly and completely below in conjunction with the figures in the embodiments of the invention. Apparently, the embodiments described are only parts of the embodiment of the invention, rather than all of the embodiments. All other embodiments obtained by those skilled in the art based on the embodiments of the invention without exerting creative effort are within the protection scope of the invention.

Embodiment One

Figure 1:
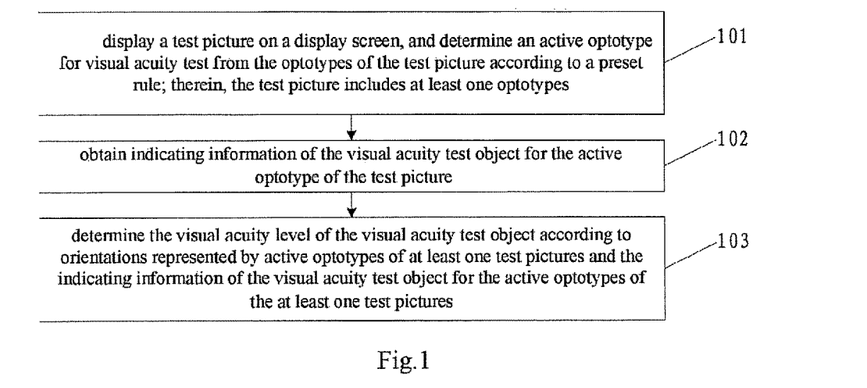
FIG. 1 is a flow schematic diagram of a visual acuity test method provided by an embodiment of the invention.

An embodiment of the invention provided a visual acuity test method, as shown in FIG. 1, which method comprises the steps of:

Step 101: displays a test picture on a display screen, and determine an active optotype for visual acuity test from the optotypes of the test picture according to a preset rule; therein, the test picture includes at least one optotypes.

Specifically, when the test picture displayed on the display screen includes one active optotype, the optotype is an active optotype for visual acuity test; when the test picture displayed on the display screen includes at least two active optotypes, the active optotype for visual acuity test can be determined from the active optotypes of the test picture according to a order from left to right, or from right to left or from the center to two sides. The multiple active optotypes determined can be displayed on the display screen individually according to a preset order, or displayed on the display screen simultaneously.

Since the preset order is adjustable freely, and the orientation of the active optotype occurring is not constant, the problem of the tested subject cheating by remembering the orientations of the optotypes of the visual acuity chart can be prevented also.

When the active optotype is determined, the active optotype is made at a highlight state, and the other inactive optotypes is made at a un-highlight state; alternatively, the active optotype and the other optotypes all are made at a highlight state, and when the active optotype is determined, the active optotype is prominently displayed with a regular graph such as a circle, a square, a rectangle etc. or a irregular graph, to differ from the other inactive optotypes.

Step 102, obtains indicating information of the visual acuity test subject for the active optotype of the test picture;

Specifically, referring to the existing visual acuity chart (E) for visual acuity test, the orientations represented by the active optotypes include left, right, up, down, and the visual acuity test subject indicates with respect to the orientations represented by the active optotypes in the test picture, and the indicating information includes orientation indicating information of the visual acuity test subject for the active optotypes.

Therein, the indicating information can be indication information sent to the visual acuity test apparatus by the visual acuity test subject with an indicator (such as a remote, a handle etc.) connected to the visual acuity test apparatus, upon indicating orientation of the active optotypes in the test picture; or can be indicating information of the visual acuity test subject for the active optotype in the test picture recognized actively by the visual acuity test apparatus.

As described in Step 101, when the multiple active optotypes for visual acuity test in the test picture are displayed on the display screen simultaneously, the visual acuity test apparatus displays a test order identifier on the display screen, which test order identifier is used for instructing the visual acuity test subject to indicate for the active optotypes in the test picture according to the direction indicated by the test order identifier. As such, the indicating information includes information of the visual acuity test subject indicating for the active optotypes in the test picture according to the direction indicated by the test order identifier. The test order identifier may be represented by an arrow, the direction indicated by which may be from left to right, from right to left, or from the center to the two sides etc.

Step 103, determine the visual acuity level of the visual acuity test subject according to orientations represented by active optotypes of at least one test pictures and the indicating information of the visual acuity test subject for the active optotypes of the at least one test pictures.

Specifically, the visual acuity test apparatus determines the visual acuity level of the visual acuity test subject, based on whether the orientations represented by the active optotypes of the at least one test pictures and the indicating information of the visual acuity test subject for the active optotypes in the as least one test pictures match with each other, that is, based on determining whether the indicating directions of the visual acuity test subject for the active optotypes in the at least one test picture are consistent with the orientations represented by the respective active optotypes.

Figure 2:
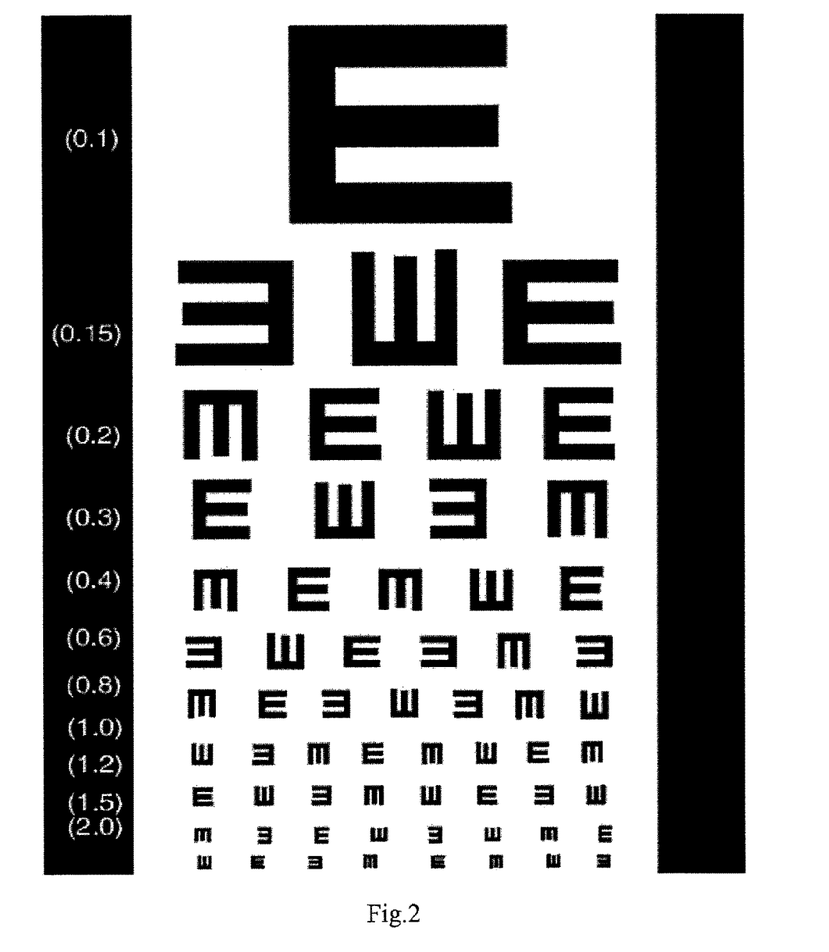
FIG. 2 is a schematic diagram of a test picture in a visual acuity test method provided by an embodiment of the invention.

As shown in FIG. 2, when the test picture displayed on the display picture includes optotypes of all levels (taking the existing standard visual acuity chart as an example), the visual acuity test apparatus determines the visual acuity level of the visual acuity test subject, by determining whether the orientations represented by the multiple optotypes in the test picture are consistent with the orientations indicated by the visual acuity test subject.

When at least two test pictures are included, and the visual acuity level to which each test picture corresponds is different from the other, when the example test apparatus detects that the indicating orientation of the visual acuity test subject for the active optotype in one test picture is the same with or different from the orientation of the active optotype in the test picture, a test picture of another visual acuity level should be switched and displayed for testing, for determining the visual acuity level of the visual acuity test subject.

Figure 3:
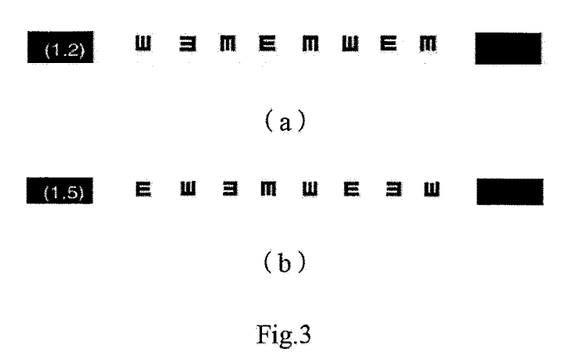
FIG. 3 is a schematic diagram of a test picture in another visual acuity test method provided by an embodiment of the invention.

Exemplarily, if a test picture of the visual acuity level of 1.2 is displayed currently on the display screen, as shown in FIG. 3(a), and the visual acuity test apparatus determines the indicating directions of the visual acuity test subject for all the optotypes in the test picture of the visual acuity level of 1.2 are the same with the orientations represented by the respective optotypes, then a test picture of a visual acuity level of 1.5 is displayed, as shown in FIG. 3(b), and if the visual acuity test apparatus determines the indicating directions of the visual acuity test subject for all the optotypes in the test picture of the visual acuity level of 1.5 are not completely the same with the orientations represented by the respective optotypes, the visual acuity level of the visual acuity test subject is determined as 1.2.

The visual acuity test method provided by the embodiments of the invention displays a test picture on a display screen, and determines an active optotype for visual acuity test from the optotypes of the test picture according to a preset rule, obtains indicating information of the visual acuity test subject for the active optotype of the test picture, and determines the visual acuity level of the visual acuity test subject according to orientations represented by active optotypes of at least one test pictures and the indicating information of the visual acuity test subject for the active optotypes of the at least one test pictures. Compared to the prior art, the visual acuity test apparatus of the embodiment of the invention does not need adding specialized tester additionally, and can prevent the problem of the tested subject cheating by remembering the orientations of the optotypes of the visual acuity chart. An automatic test of the visual acuity level of the visual acuity test subject may be realized only according to the represented orientation of the active optotype of the displayed test picture and the indicating information of the visual acuity test subject for the active optotype, solving the problem of complex operation of the existing visual acuity test solution.

Embodiment Two

Figure 4:
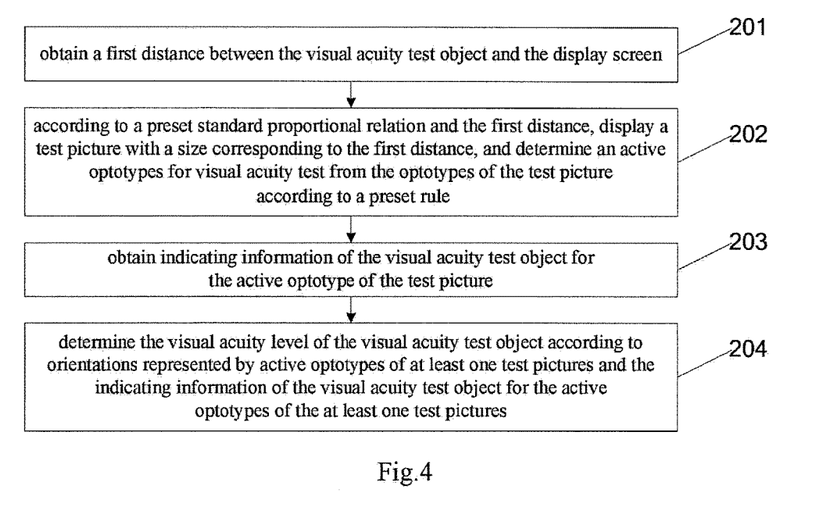
FIG. 4 is a flow schematic diagram of another visual acuity test method provided by an embodiment of the invention.

The embodiment of the invention provides a visual acuity test method, which for example is applied in a visual acuity test apparatus with a display screen, as shown in FIG. 4, which method comprise the steps of:

Step 201, obtain a first distance between the visual acuity test subject and the display screen.

Specifically, the distance between the visual acuity test subject and the display screen may be measured by means of microwave, infrared or ultrasonic wave etc. technologies.

Optionally, for ensuring the matching of each visual acuity test subject and his visual acuity test level, the identity information (such as head portrait or fingerprint etc.) for identifying the visual acuity test subject may be stored previously in the visual acuity test apparatus, and after that, when a visual acuity test subject performs the visual acuity test, the visual acuity test apparatus obtains the identity information of the visual acuity test subject, and matches it with the identity information of the visual acuity test subject prestored, and after the identity information is matched successfully, obtains the first distance between the visual acuity test subject and the display screen.

Step 202, according to a preset standard proportional relation and the first distance, display a test picture with a size corresponding to the first distance, and determines an active optotypes for visual acuity test from the optotypes of the test picture according to a preset rule.

Therein, the preset standard proportional relation includes: a standard distance between the visual acuity subject and the display screen, and a standard test picture size corresponding to the standard distance.

In the prior art, the visual acuity test subject should stand at a position at a standard distance (normally 5 m) of a standard visual acuity test chart, then can performs the visual acuity test. Whereas, the visual acuity test apparatus in the invention can display a test picture with a size corresponding to the first distance, according to the first distance between the visual acuity test subject and the display screen. Exemplarily, the side of the standard visual acuity test chart is represented by A. When the visual acuity test apparatus detects that the first distance between the visual acuity test subject and the display screen is 2.5 m, according to the preset standard proportional relation, i.e. $2.5/B=5/A$, it can be calculated that, a test picture of size B should be displayed when the distance is 2.5 m; when the visual acuity test apparatus detects that the first distance between the visual acuity test subject and the display screen is 7.5 m, according to the preset standard proportional relation, i.e. $7.5/C=5/A$, it can be calculated that, a test picture of size C should be displayed when the distance is 7.5 m.

As can be known from the above description, when the first distance between the visual acuity test subject and the display screen is smaller than the standard distance, the size of the test picture displayed on the display screen is reduced; when the first distance between the visual acuity test subject and the display screen is larger than the standard distance, the size of the test picture displayed on the display screen is increased. As such, the visual acuity test apparatus may adjust the size of the test picture to be displayed adaptively according to the first distance.

Step 203, obtain indicating information of the visual acuity test subject for the active optotype of the test picture.

Step 204, determine the visual acuity level of the visual acuity test subject according to orientations represented by active optotypes of at least one test pictures and the indicating information of the visual acuity test subject for the active optotypes of the at least one test pictures.

For the details of the steps 203 and 204, the steps 103 and 104 in the embodiment one can be referred, which would not be described repeatedly.

The visual acuity test method provided by the embodiments of the invention obtains the first distance between the visual acuity test subject and the display screen, and displays a test picture with a size corresponding to the first distance on a display screen, and determines an active optotype for visual acuity test from the optotypes of the test picture according to a preset rule, obtains indicating information of the visual acuity test subject for the active optotype of the test picture, and determines the visual acuity level of the visual acuity test subject according to orientations represented by active optotypes of at least one test pictures and the indicating information of the visual acuity test subject for the active optotypes of the at least one test pictures. Compared to the prior art, the visual acuity test apparatus of the embodiment of the invention automatically adjusts the size of the test picture to be displayed according to the first distance, and does not need adding specialized tester additionally, and can prevent the problem of the tested subject cheating by remembering the orientations of the optotypes of the visual acuity chart. An automatic test of the visual acuity level of the visual acuity test subject may be realized only according to the represented orientation of the active optotype of the displayed test picture and the indicating information of the visual acuity test subject for the active optotype, solving the problem of complex operation of the existing visual acuity test solution.

Embodiment Three

Figure 5A:
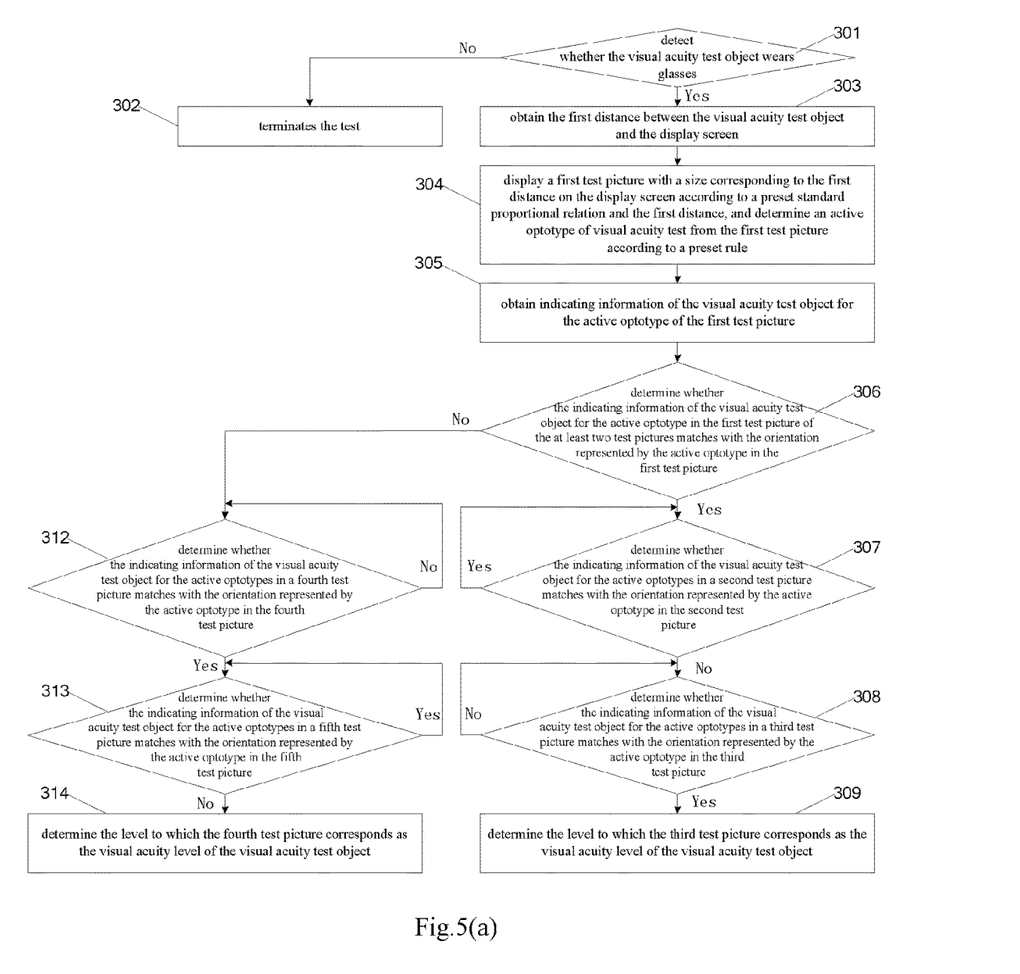
Figure 5B:
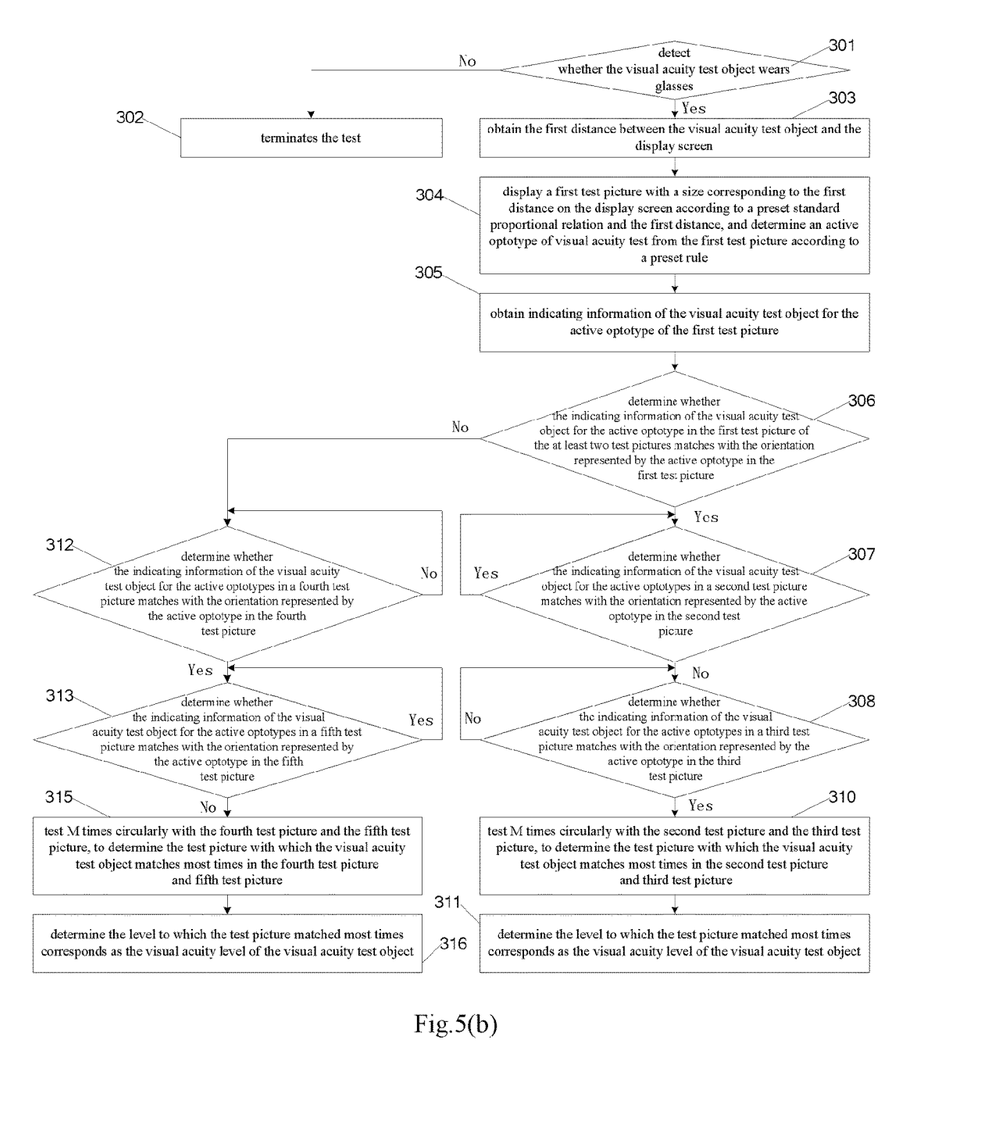

The embodiment of the invention provides a visual acuity test method, which for example is applied in a visual acuity test apparatus with a display screen, and the visual acuity test apparatus comprises as least two test pictures, each of which corresponds to a different visual acuity level, and as shown in FIGS. 5(a) and 5(b), the method comprises the steps of:

Step 301, detect whether the visual acuity test subject wears glasses.

Specifically, the visual acuity test apparatus may determine whether the visual acuity test subject wears glasses by detecting the reflectance of light of the eyes of the visual acuity test subject. Exemplarily, the visual acuity test apparatus emits a light beam to the eyes of the visual acuity test subject, and when detects that the reflectance of light of the eyes of the visual acuity test subject is larger than a preset value, determines that the visual acuity test subject wears glasses; if detects that the reflectance of light of the eyes of the visual acuity test subject is smaller than a preset value, determines that the visual acuity test subject does not wear glasses; therein, the preset value can be set according to the range of lowest reflectance of light of various different glasses. Of course, other solutions which can detect whether the user wears glasses are feasible, which are not defined uniquely here.

If it is detected that the visual acuity test subject wears glasses, perform step 302; if it is detected that the visual acuity test subject does not wear glasses, perform step 303.

Step 302, if it is detected that the visual acuity test subject wears glasses, terminate the test or controls the visual acuity test apparatus to stop working.

Step 303, if it is detected that the visual acuity test subject does not wear glasses, obtain the first distance between the visual acuity test subject and the display screen.

Step 304, display a first test picture with a size corresponding to the first distance on the display screen according to a preset standard proportional relation and the first distance, and determine an active optotype of visual acuity test from the first test picture according to a preset rule.

Step 305, obtain indicating information of the visual acuity test subject for the active optotype of the first test picture.

For the details of the steps 302-305, the descriptions of respective steps in Embodiment one and two can be referred, which would not be repeated here.

Step 306, determine whether the indicating information of the visual acuity test subject for the active optotype in the first test picture of the at least two test pictures matches with the orientation represented by the active optotype in the first test picture.

If the indicating information of the visual acuity test subject for the active optotypes in a first test picture of the at least two test pictures matches with the orientation represented by the active optotype in the first test picture, turn to step 307; if the indicating information of the visual acuity test subject for the active optotypes in a first test picture of the at least two test pictures does not match with the orientation represented by the active optotype in the first test picture, turn to step 312.

Step 307, if matched, determine whether the indicating information of the visual acuity test subject for the active optotypes in a second test picture matches with the orientation represented by the active optotype in the second test picture.

Therein, the second test picture is a test picture having a visual acuity level different from that of the first test picture by N visual acuity levels, and the visual acuity level of the second test picture is higher than that of the first test picture, N being a positive integer.

If the indicating information of the visual acuity test subject for the active optotypes in the second test pictures matches with the orientation represented by the active optotype in the second test picture, consider the second test picture as the first test picture, and continue to step 307, until the indicating information of the visual acuity test subject for the active optotypes in the second test pictures does not match with the orientation represented by the active optotype in the second test picture, and then turns to step 308.

Step 308, if not matched, determine whether the indicating information of the visual acuity test subject for the active optotypes in a third test picture matches with the orientation represented by the active optotype in the third test picture.

Therein, the third test picture is a test picture having a visual acuity level adjacent with that of the second test picture, and the visual acuity level of the third test picture is lower than that of the second test picture.

If the indicating information of the visual acuity test subject for the active optotypes in the third test pictures does not match with the orientation represented by the active optotype in the third test picture, consider the third test picture as the second test picture, and continue to step 308, until the indicating information of the visual acuity test subject for the active optotypes in the third test pictures matches with the orientation represented by the active optotype in the third test picture, and then employ two ways for determining the visual acuity level of the visual acuity test subject. One way is directly determining the level to which the third test picture corresponds as the visual acuity level of the visual acuity test subject, that is turning to step 309, as shown in FIG. 5(a). Another way is testing several times circularly with the second test picture and the third test picture, to reduce misjudgment, improve the accuracy of visual acuity test, that is turning to steps 301-311, as shown in FIG. 5(b).

Step 309, if matched, determine the level to which the third test picture corresponds as the visual acuity level of the visual acuity test subject.

Step 310, if matched, test M times circularly with the second test picture and the third test picture, to determine the test picture with which the visual acuity test subject matches most times in the second test picture and third test picture.

To reduce the probability of misjudgment, the tests may be performed M times circularly with the second test picture and the third test picture, to determine the test picture with which the visual acuity test subject matches most times in the second test picture and third test picture.

Step 311, determine the level to which the test picture matched most times corresponds as the visual acuity level of the visual acuity test subject.

When the visual acuity level of the visual acuity test subject is determined, the visual acuity test apparatus may inform the visual acuity test subject that the visual acuity test is ended by a way of voice or displaying on the screen (such as: Test ended). It is also possible to inform the visual acuity level of the visual acuity test subject to the visual acuity test subject by a way of voice or displaying on the screen, such as "Your visual acuity is 0.8!". Of course, the visual acuity level of the visual acuity test subject may be printed and output.

Next, take a specific implementation for an example. Specifically, the visual acuity test apparatus detects that the user does not wear glasses, and displays a test picture with a corresponding size according to the first distance between the user and the display screen. The first test picture is a test picture to which an average visual acuity level of a normal user corresponds. The embodiment of the invention takes the average visual acuity level of 0.6 as an example.

With N=1, the pattern in the test picture being an "E" letter in a standard visual acuity test chart, the visual acuity test apparatus displaying the active optotypes in order from left to right, and the user indicating according to the order from left to right as an example, if the visual acuity level to which the currently displayed test picture corresponds is 0.6, and the visual acuity test apparatus determines the indicating directions of the visual acuity test subject for all of the visual optotypes in the test picture of a visual acuity level of 0.6 are the same with the orientations represented by the respective optotypes, then displays a test picture of a visual acuity level of 0.8; if the visual acuity test apparatus determines the indicating directions of the visual acuity test subject for all of the visual optotypes in the test picture of a visual acuity level of 0.8 are the same with the orientations represented by the respective optotypes, displays a test picture of a visual acuity level of 1.0; if the visual acuity test apparatus determines the indicating directions of the visual acuity test subject for all of the visual optotypes in the test picture of a visual acuity level of 1.0 are the same with the orientations represented by the respective optotypes, displays a test picture of a visual acuity level of 1.2; if the visual acuity test apparatus determines the indicating directions of the visual acuity test subject for all of the visual optotypes in the test picture of a visual acuity level of 1.2 are not completely the same with the orientations represented by the respective optotypes, displays a test picture of a visual acuity level of 1.0; if the visual acuity test apparatus determines the indicating directions of the visual acuity test subject for all of the visual optotypes in the test picture of a visual acuity level of 1.0 are the same with the orientations represented by the respective optotypes, performs 3 times of tests circularly with the test picture of a visual acuity level of 1.0 and the test picture of a visual acuity level of 1.2. If the user can completely correctly indicate for the test picture of a visual acuity level of 1.0, and can not completely correctly indicate for the test picture of a visual acuity of 1.2, then the visual acuity level of the user is determined as 1.0.

With N=2, the pattern in the test picture being an "E" letter in a standard visual acuity test chart, the visual acuity test apparatus displaying the active optotypes in order from left to right, and the user indicating according to the order from left to right as an example, if the visual acuity level to which the currently displayed test picture corresponds is 0.6, and the visual acuity test apparatus determines the indicating directions of the visual acuity test subject for all of the visual optotypes in the test picture of a visual acuity level of 0.6 are the same with the orientations represented by the respective optotypes, then displays a test picture of a visual acuity level of 1.0; if the visual acuity test apparatus determines the indicating directions of the visual acuity test subject for all of the visual optotypes in the test picture of a visual acuity level of 1.0 are the same with the orientations represented by the respective optotypes, displays a test picture of a visual acuity level of 1.5; if the visual acuity test apparatus determines the indicating directions of the visual acuity test subject for all of the visual optotypes in the test picture of a visual acuity level of 1.5 are not completely the same with the orientations represented by the respective optotypes, displays a test picture of a visual acuity level of 1.2; if the visual acuity test apparatus determines the indicating directions of the visual acuity test subject for all of the visual optotypes in the test picture of a visual acuity level of 1.2 are not completely the same with the orientations represented by the respective optotypes, displays a test picture of a visual acuity level of 1.0; if the visual acuity test apparatus determines the indicating directions of the visual acuity test subject for all of the visual optotypes in the test picture of a visual acuity level of 1.0 are completely the same with the orientations represented by the respective optotypes, performs 3 times of tests circularly with the test picture of a visual acuity level of 1.0 and the test picture of a visual acuity level of 1.2. If the user can completely correctly indicate for the test picture of a visual acuity level of 1.0, and can not completely correctly indicate for the test picture of a visual acuity of 1.2, then the visual acuity level of the user is determined as 1.0.

With N being a random number, the pattern in the test picture being an "E" letter in a standard visual acuity test chart, the visual acuity test apparatus displaying the active optotypes in order from left to right, and the user indicating according to the order from left to right as an example, if the visual acuity level to which the currently displayed test picture corresponds is 0.6, and the visual acuity test apparatus determines the indicating directions of the visual acuity test subject for all of the visual optotypes in the test picture of a visual acuity level of 0.6 are the same with the orientations represented by the respective optotypes, then displays a test picture of a visual acuity level of 0.8; if the visual acuity test apparatus determines the indicating directions of the visual acuity test subject for all of the visual optotypes in the test picture of a visual acuity level of 0.8 are the same with the orientations represented by the respective optotypes, displays a test picture of a visual acuity level of 1.2; if the visual acuity test apparatus determines the indicating directions of the visual acuity test subject for all of the visual optotypes in the test picture of a visual acuity level of 1.2 are not completely the same with the orientations represented by the respective optotypes, displays a test picture of a visual acuity level of 1.0; if the visual acuity test apparatus determines the indicating directions of the visual acuity test subject for all of the visual optotypes in the test picture of a visual acuity level of 1.0 are completely the same with the orientations represented by the respective optotypes, performs 3 times of tests circularly with the test picture of a visual acuity level of 1.0 and the test picture of a visual acuity level of 1.2. If the user can completely correctly indicate for the test picture of a visual acuity level of 1.0, and can not completely correctly indicate for the test picture of a visual acuity of 1.2, then the visual acuity level of the user is determined as 1.0.

Step 312, if not matched, determine whether the indicating information of the visual acuity test subject for the active optotype in the fourth test picture matches with the orientation represented by the active optotype in the fourth test picture.

Therein, the fourth test picture is a test picture having a visual acuity level different from that of the first test picture by P visual acuity levels, and the visual acuity level of the fourth test picture is lower than that of the first test picture, the P being a negative integer;

If the indicating information of the visual acuity test subject for the active optotypes in the fourth test pictures matches with the orientation represented by the active optotype in the fourth test picture, then consider the fourth test picture as the first test picture, and continue to step 312, until the visual acuity test apparatus determines that the indicating information of the visual acuity test subject for the active optotypes in the fourth test pictures does not match with the orientation represented by the active optotype in the fourth test picture, and then turn to step 313.

Step 313, if matched, determine whether the indicating information of the visual acuity test subject for the active optotypes in a fifth test picture matches with the orientation represented by the active optotype in the fifth test picture.

Therein, the fifth test picture is a test picture having a visual acuity level adjacent with that of the fourth test picture, and the visual acuity level of the fifth test picture is higher than that of the fourth test picture;

If the indicating information of the visual acuity test subject for the active optotypes in the fifth test pictures does not match with the orientation represented by the active optotype in the fifth test picture, then consider the fifth test picture as the fourth test picture, and continue to step 313, until the visual acuity test apparatus determines that the indicating information of the visual acuity test subject for the active optotypes in the fifth test pictures matches with the orientation represented by the active optotype in the fifth test picture, and then employ two ways for determining the visual acuity level of the visual acuity test subject. One way is directly determining the level to which the fourth test picture corresponds as the visual acuity level of the visual acuity test subject, that is turning to step 314, as shown in FIG. 5(*a*). Another way is testing several times circularly with the fourth test picture and the fifth test picture, to reduce misjudgment, improve the accuracy of visual acuity test, that is turning to steps 315-316, as shown in FIG. 5(*b*).

Step 314, if not matched, determine the level to which the fourth test picture corresponds as the visual acuity level of the visual acuity test subject.

Step 315, if not matched, test M times circularly with the fourth test picture and the fifth test picture, to determine the test picture with which the visual acuity test subject matches most times in the fourth test picture and fifth test picture.

For reducing the probability of misjudgment, it is possible that perform M times of tests circularly with the fourth test picture and the fifth test picture, to determine the test picture with which the visual acuity test subject matches most times in the fourth test picture and fifth test picture.

Step 316, determine the level to which the test picture matched most times corresponds as the visual acuity level of the visual acuity test subject.

Next, take a specific implementation for an example. Specifically, the visual acuity test apparatus detects that the user does not wear glasses, and displays a test picture with a corresponding size according to the first distance between the user and the display screen. The first test picture is a test picture to which an average visual acuity level of a normal user corresponds. The embodiment of the invention takes the average visual acuity level of 0.6 as an example.

With P=−1, the pattern in the test picture being an "E" letter in a standard visual acuity test chart, the visual acuity test apparatus displaying the active optotypes in a order from left to right, and the user indicating according to the order from left to right as an example, if the visual acuity level to which the currently displayed test picture corresponds is 0.6, and the visual acuity test apparatus determines the indicating directions of the visual acuity test subject for all of the visual optotypes in the test picture of a visual acuity level of 0.6 are not completely the same with the orientations represented by the respective optotypes, then displays a test picture of a visual acuity level of 0.4; if the visual acuity test apparatus determines the indicating directions of the visual acuity test subject for all of the visual optotypes in the test picture of a visual acuity level of 0.4 are not completely the same with the orientations represented by the respective optotypes, displays a test picture of a visual acuity level of 0.3; if the visual acuity test apparatus determines the indicating directions of the visual acuity test subject for all of the visual optotypes in the test picture of a visual acuity level of 0.3 are not completely the same with the orientations represented by the respective optotypes, displays a test picture of a visual acuity level of 0.2; if the visual acuity test apparatus determines the indicating directions of the visual acuity test subject for all of the visual optotypes in the test picture of a visual acuity level of 0.2 are completely the same with the orientations represented by the respective optotypes, displays a test picture of a visual acuity level of 0.3; if the visual acuity test apparatus determines the indicating directions of the visual acuity test subject for all of the visual optotypes in the test picture of a visual acuity level of 0.3 are not completely the same with the orientations represented by the respective optotypes, performs 3 times of tests circularly with the test picture of a visual acuity level of 0.2 and the test picture of a visual acuity level of 0.3. If the user can completely correctly indicate for the test picture of a visual acuity level of 0.2, and can not completely correctly indicate for the test picture of a visual acuity of 0.3, then the visual acuity level of the user is determined as 0.2.

With P=−2, the pattern in the test picture being an "E" letter in a standard visual acuity test chart, the visual acuity test apparatus displaying the active optotypes in a order from left to right, and the user indicating according to the order from left to right as an example, if the visual acuity level to which the currently displayed test picture corresponds is 0.6, and the visual acuity test apparatus determines the indicating directions of the visual acuity test subject for all of the visual optotypes in the test picture of a visual acuity level of 0.6 are not completely the same with the orientations represented by the respective optotypes, then displays a test picture of a visual acuity level of 0.3; if the visual acuity test apparatus determines the indicating directions of the visual acuity test subject for all of the visual optotypes in the test picture of a visual acuity level of 0.3 are not completely the same with the orientations represented by the respective optotypes, displays a test picture of a visual acuity level of 0.15; if the visual acuity test apparatus determines the indicating directions of the visual acuity test subject for all of the visual optotypes in the test picture of a visual acuity level of 0.15 are completely the same with the orientations represented by the respective optotypes, displays a test picture of a visual acuity level of 0.2; if the visual acuity test apparatus determines the indicating directions of the visual acuity test subject for all of the visual optotypes in the test picture of a visual acuity level of 0.2 are the same with the orientations represented by the respective optotypes, displays a test picture of a visual acuity level of 0.3; if the visual acuity test apparatus determines the indicating directions of the visual acuity test subject for all of the visual optotypes in the test picture of a visual acuity level of 0.3 are not completely the same with the orientations represented by the respective optotypes, performs 3 times of tests circularly with the test picture of a visual acuity level of 0.2 and the test picture of a visual acuity level of 0.3. If the user can completely correctly indicate for the test picture of a visual acuity level of 0.2, and can not completely correctly indicate for the test picture of a visual acuity of 0.3, then the visual acuity level of the user is determined as 0.2.

With P being a random number, the pattern in the test picture being an "E" letter in a standard visual acuity test chart, the visual acuity test apparatus displaying the active optotypes in order from left to right, and the user indicating according to the order from left to right as an example, if the visual acuity level to which the currently displayed test picture corresponds is 0.6, and the visual acuity test apparatus determines the indicating directions of the visual acuity test subject for all of the visual optotypes in the test picture of a visual acuity level of 0.6 are not completely the same with the orientations represented by the respective optotypes, then displays a test picture of a visual acuity level of 0.4; if the visual acuity test apparatus determines the indicating directions of the visual acuity test subject for all of the visual optotypes in the test picture of a visual acuity level of 0.4 are not completely the same with the orientations represented by the respective optotypes, displays a test picture of a visual acuity level of 0.2; if the visual acuity test apparatus determines the indicating directions of the visual acuity test subject for all of the visual optotypes in the test picture of a visual acuity level of 0.2 are completely the same with the orientations represented by the respective optotypes, displays a test picture of a visual acuity level of 0.3; if the visual acuity test apparatus determines the indicating directions of the visual acuity test subject for all of the visual optotypes in the test picture of a visual acuity level of 0.3 are not completely the same with the orientations represented by the respective optotypes, performs 3 times of tests circularly with the test picture of a visual acuity level of 0.2 and the test picture of a visual acuity level of 0.3. If the user can completely correctly indicate for the test picture of a visual acuity level of 0.2, and can not completely correctly indicate for the test picture of a visual acuity of 0.3, then the visual acuity level of the user is determined as 0.2.

The visual acuity test method provided by the embodiments of the invention obtains the first distance between the visual acuity test subject and the display screen when detects that the visual acuity test subject does not wear glasses, and displays a test picture with a size corresponding to the first distance on a display screen, and determines an active optotype for visual acuity test from the optotypes of the test picture according to a preset rule, obtains indicating information of the visual acuity test subject for the active optotype of the test picture, and determines the visual acuity level of the visual acuity test subject according to orientations represented by active optotypes of at least one test pictures and the indicating information of the visual acuity test subject for the active optotypes of the at least one test pictures. Compared to the prior art, the visual acuity test apparatus of the embodiment of the invention automatically adjusts the size of the test picture to be displayed according to the first distance, and does not need adding specialized tester additionally, and can prevent the problem of the tested subject cheating by remembering the orientations of the optotypes of the visual acuity chart. An automatic test of the visual acuity level of the visual acuity test subject may be realized only according to the represented orientation of the active optotype of the displayed test picture and the indicating information of the visual acuity test subject for the active optotype, solving the problem of complex operation of the existing visual acuity test solution.

Embodiment Four

Figure 6:
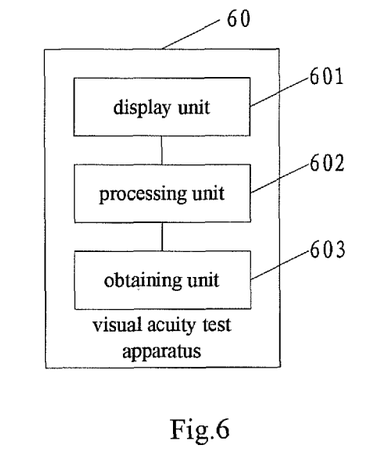
FIG. 6 is a structural schematic diagram of a visual acuity test apparatus provided by an embodiment of the invention.

The embodiment of the invention provides a visual acuity test apparatus as shown in FIG. 6, which visual acuity test apparatus 60 comprises: a display unit 601, a processing unit 602, a obtaining unit 603; therein, The display unit 601 is used for displaying a test picture which includes at least one optotypes;

The processing unit 602 is used for determining an active optotype for visual acuity test from the optotypes of the test picture according to a preset rule;

The obtaining unit 603 is used for obtaining indicating information of the visual acuity test subject for the active optotype of the test picture;

The processing unit 602 is further used for determine the visual acuity level of the visual acuity test subject according to orientations represented by active optotypes of at least one test pictures and the indicating information of the visual acuity test subject for the active optotypes of the at least one test pictures.

Figure 7:
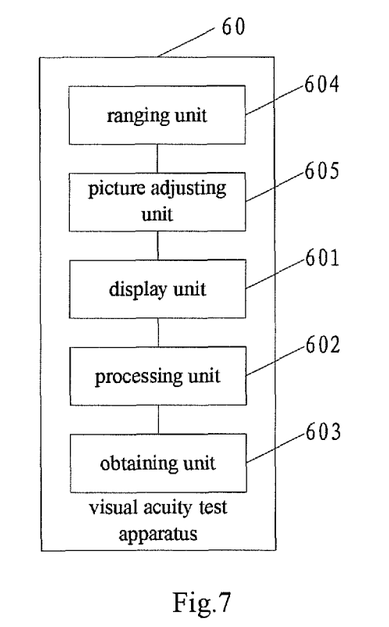
FIG. 7 is a structural schematic diagram of another visual acuity test apparatus provided by an embodiment of the invention.

Further, as shown in FIG. 7, the apparatus 60 further comprises:

a ranging unit 604, for obtaining a first distance between the visual acuity test subject and the display screen before the display unit 601 displaying the test picture;

a picture adjusting unit 605, for adjusting the test picture as a test picture with a size corresponding to the first distance according to a preset standard proportional relation and the first distance;

The display unit 601 is further used for displaying the test picture with a size corresponding to the first distance; therein, the preset standard proportional relation includes: a standard distance between the visual acuity subject and the display screen, and a standard test picture size corresponding to the standard distance.

Figure 8:
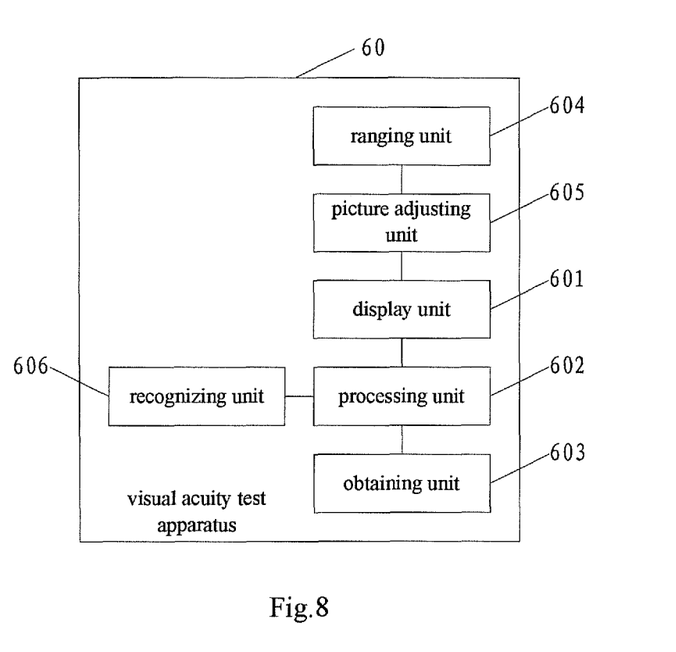
FIG. 8 is a structural schematic diagram of another visual acuity test apparatus provided by an embodiment of the invention.

Further, as shown in FIG. 8, the apparatus 60 further comprises:

a recognizing unit 606, for detecting whether the visual acuity test subject wears glasses before the ranging unit 604 obtaining the first distance between the visual acuity test subject and the display screen;

the processing unit 602 is further used for if the recognizing unit 606 detects that the visual acuity test subject wears glasses, controlling the visual acuity apparatus to stop working.

The visual acuity test apparatus provided by the embodiments of the invention displays a test picture on a display screen, and determines an active optotype for visual acuity test from the optotypes of the test picture according to a preset rule, obtains indicating information of the visual acuity test subject for the active optotype of the test picture, and determines the visual acuity level of the visual acuity test subject according to orientations represented by active optotypes of at least one test pictures and the indicating information of the visual acuity test subject for the active optotypes of the at least one test pictures. Compared to the prior art, the visual acuity test apparatus of the embodiment of the invention does not need adding specialized tester additionally, and may realize an automatic test of the visual acuity level of the visual acuity test subject only according to the represented orientation of the active optotype of the displayed test picture and the indicating information of the visual acuity test subject for the active optotype, solving the problem of complex operation of the existing visual acuity test solution.

Figure 9:
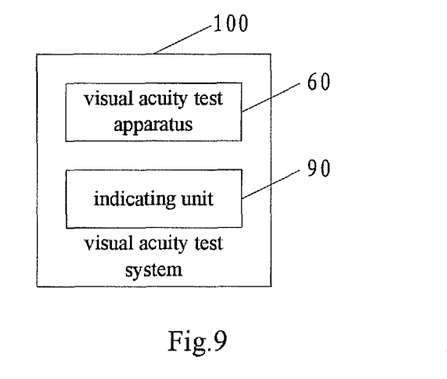
FIG. 9 is a structural schematic diagram of a visual acuity test system provided by an embodiment of the invention.

The embodiment of the invention further provides a visual acuity test system as shown in FIG. 9, which visual acuity test system 100 comprises: the visual acuity test apparatus 60 as shown in any one of FIGS. 6-8, and an indicating unit 90. Therein, the indicating unit 90 is used for sending the indicating information of the visual acuity test subject for the active optotype of the at least one test picture to the visual acuity test apparatus. The indicating unit 90 may connect to the visual acuity test apparatus 60 wirelessly or by a hardwire. Exemplarily, the indicating unit 90 may be a remote, a handle or a touch screen, etc. For the functional description of the visual acuity test apparatus 60, the content recited in the above embodiments can be referred, which would not be repeated here.

The visual acuity test system provided by the embodiments of the invention displays a test picture on a display screen, and determines an active optotype for visual acuity test from the optotypes of the test picture according to a preset rule, obtains indicating information of the visual acuity test subject for the active optotype of the test picture, and determines the visual acuity level of the visual acuity test subject according to orientations represented by active optotypes of at least one test pictures and the indicating information of the visual acuity test subject for the active optotypes of the at least one test pictures. Compared to the prior art, the visual acuity test apparatus of the embodiment of the invention does not need adding specialized tester additionally, and may realize an automatic test of the visual acuity level of the visual acuity test subject only according to the represented orientation of the active optotype of the displayed test picture and the indicating information of the visual acuity test subject for the active optotype, solving the problem of complex operation of the existing visual acuity test solution.

Those skilled in the art can understand that, all or parts of the method embodiments can be performed by hardware related to a program instruction, and the program can be stored in a computer readable storage media, and when the program is executed, the steps comprising the above method embodiments can be performed; the storage media comprise ROM, RAM, magnetic disk or optical disk and various media which can store the program codes etc.

The above described are only specific embodiments of the invention, and the protection scope of the invention is not limited to this. Any variation or substitution easily thought of by those skilled in the art from the technical scope disclosed by the invention should be covered within the protection scope of the invention. Therefore, the protection scope of the invention should be subjected to the protection scope of the claims. The wording "comprise" or "comprising" in the claims does not exclude the presence of other elements or steps which are not listed in the claims. The wording "a" or "an" ahead of an element does not exclude the presence of a plurality of such elements. The mere fact that certain measures are recited in mutually different dependent claims does not indicate that a combination of these measures cannot be used to advance.

The invention claimed is:

1. A visual acuity test method, which comprises the steps of:
displaying a test picture which includes at least one optotype on a display screen, and determines an active optotype for visual acuity test from the at least one optotype of the test picture;
obtaining, from the visual acuity test subject, indication information for the active optotype of the test picture; and
determining the visual acuity level of the visual acuity test subject according to orientations represented by the active optotype of the test picture and the indication information for the active optotype of the test picture;
wherein at least two test pictures are displayed, each of which corresponds to a different visual acuity level, and wherein the at least two test pictures are displayed individually on the display screen;
wherein, before the step of displaying the test picture on the display screen, the method further comprises:
obtaining a first distance between the visual acuity test subject and the display screen;
the step of displaying the test picture on the display screen comprises: according to a preset standard proportional relation and the first distance, proportionally determining a size corresponding to the first distance and adaptively adjusting the test picture with the size corresponding to the first distance; wherein
the preset standard proportional relation includes: a standard distance between the visual acuity test subject and the display screen, and a standard test picture size corresponding to the standard distance.

2. The method according to claim 1, wherein, the step of determining the visual acuity level of the visual acuity test subject according to orientations represented by the active optotype of the test picture and the indication information for the active optotype of the test picture comprises:
determining whether the indication information for the active optotype in a first test picture of the at least two test pictures matches with the orientation represented by the active optotype in the first test picture; wherein
if the indication information for the active optotype in a first test picture of the at least two test pictures matches with the orientation represented by the active optotype in the first test picture, determining whether the indication information for the active optotype in a second test picture of the at least two test pictures matches with the orientation represented by the active optotype in the second test picture; wherein the second test picture is a test picture has a visual acuity level different from that of the first test picture by N visual acuity levels, and the visual acuity level of the second test picture is higher than that of the first test picture, wherein N is a positive integer; wherein
if the indication information for the active optotype in the second test picture does not match with the orientation represented by the active optotype in the second test picture, determining whether the indication information for the active optotype in a third test picture of the at least two test pictures matches with the orientation represented by the active optotype in the third test picture; wherein the third test picture is a test picture has a visual acuity level adjacent with that of the second test picture, and wherein the visual acuity level of the third test picture is lower than that of the second test picture; and wherein
if the indication information for the active optotype in the third test picture matches with the orientation represented by the active optotype in the third test picture, determining the visual acuity level to which the third test picture corresponds as the visual acuity level of the visual acuity test subject.

3. The method according to claim 2, wherein, the method further comprises: if the indication information for the active optotype in the third test picture of the at least two test pictures matches with the orientation represented by the active optotype in the third test picture, performing M times of tests with the second test picture and the third test picture, determines a test picture matched more times by the visual acuity test subject from the second test picture and the third test picture, M being a natural number; and determining the level to which the test picture matched more times by the visual acuity test subject corresponds as the visual acuity level of the visual acuity test subject.

4. The method according to claim 2, wherein the method further comprises, if the indication information for the active optotype in the first test picture does not match with the orientation represented by the active optotype in the first test picture:

determining whether the indication information for the active optotype in a fourth test picture of the at least two test pictures matches with the orientation represented by the active optotype in the fourth test picture; wherein the fourth test picture is a test picture having a visual acuity level different from that of the first test picture by P visual acuity levels, and the visual acuity level of the fourth test picture is lower than that of the first test picture, and wherein P is a negative integer; wherein if the indication information for the active optotype in the fourth test picture matches with the orientation represented by the active optotype in the fourth test picture, determining whether the indication information for the active optotype in a fifth test picture of the at least two test pictures matches with the orientation represented by the active optotype in the fifth test picture; wherein the fifth test picture is a test picture having a visual acuity level adjacent with that of the fourth test picture, and wherein the visual acuity level of the fifth test picture is higher than that of the fourth test picture; and if the indication information for the active optotype in the fifth test picture does not match with the orientation represented by the active optotype in the fifth test picture, determining the visual acuity level to which the fourth test picture corresponds as the visual acuity level of the visual acuity test subject.

5. The method according to claim 4, wherein the method further comprises: if the indication information for the active optotype in the fifth test picture does not match with the orientation represented by the active optotype in the fifth test picture:

performing M times of tests with the fourth test picture and the fifth test picture, determines a test picture matched more times by the visual acuity test subject from the fourth test picture and the fifth test picture; and determining the level to which the test picture matched more times by the visual acuity test subject corresponds as the visual acuity level of the visual acuity test subject.

6. The method according to claim 3, wherein, M is 2 or 3.

7. The method according to claim 5, wherein, M is 2 or 3.

8. The method according to claim 1, wherein, if there are multiple active optotypes, displaying the active optotypes individually on the display screen according to a preset order.

9. The method according to claim 8, wherein the preset order is adjustable freely.

10. The method according to claim 1, wherein, if there are multiple active optotypes, display the active optotypes simultaneously on the display screen, and display on the display screen a test order identifier for instructing the visual acuity test subject to provide the indication information for the active optotype in the test picture according to the direction indicated by the test order identifier.

11. The method according to claim 1, wherein, when the active optotype is determined, making the active optotype at a highlight state, and making the other inactive optotypes at a un-highlight state; or, when the active optotype is determined, making the active optotype and the other optotypes all at a highlight state, and prominently displaying the active optotype in a graph to differ from the other inactive optotypes.

12. A visual acuity test apparatus, which comprises:

a display unit, for displaying a test picture which includes at least one optotype;

a processing unit, for determining an active optotype for visual acuity test from the at least one optotype of the test picture; and an obtaining unit, for obtaining from the visual acuity test subject indication information for the active optotype of the test picture; wherein the processing unit is further used for determining the visual acuity level of the visual acuity test subject according to orientations represented by the active optotype of the test picture and the indication information for the active optotype of the picture;

wherein at least two test pictures are displayed, each of which corresponds to a different visual acuity level, and wherein the at least two test pictures are displayed individually on the display screen;

wherein the apparatus further comprises:

a ranging unit, for obtaining a first distance between the visual acuity test subject and the display screen before the display unit displays the test picture; and a picture adjusting unit, for proportionally determining a size corresponding to the first distance and adaptively adjusting the test picture with the size corresponding to the first distance according to a preset standard proportional relation and the first distance;

wherein the display unit is further used for displaying the test picture with a size corresponding to the first distance; the preset standard proportional relation includes: a standard distance between the visual acuity test subject and the display screen, and a standard test picture size corresponding to the standard distance.

13. A visual acuity test system, which comprises the visual acuity test apparatus according to claim 12, and an indicating unit for sending the indication information for the active optotype of the picture to the visual acuity test apparatus.

14. A visual acuity test system, which comprises the visual acuity test apparatus according to claim 12, and an indicating unit for sending the indication information for the active optotype of the test picture to the visual acuity test apparatus.

* * * * *